US005095096A

United States Patent [19]

Miki et al.

[11] Patent Number: 5,095,096

[45] Date of Patent: Mar. 10, 1992

[54] FUSED PROTEIN COMPRISING LYMPHOTOXIN

[75] Inventors: Tetsuzo Miki, Abiko; Seishi Kato, Sagamihara; Hiroshi Osada, Machida, all of Japan

[73] Assignees: Sagami Chemical Research Center, Tokyo; Central Glass Company, Ltd., Yamaguchi; Hodogaya Chemical Co., Ltd., Tokyo; Nippon Soda Company, Ltd., Tokyo; Nissan Chemical Industries, Ltd., Tokyo; Tosoh Corporation, Yamaguchi, all of Japan

[21] Appl. No.: 304,842

[22] PCT Filed: May 28, 1988

[86] PCT No.: PCT/JP88/00525

§ 371 Date: Jan. 24, 1989

§ 102(e) Date: Jan. 24, 1989

[87] PCT Pub. No.: WO88/09343

PCT Pub. Date: Dec. 1, 1988

[30] Foreign Application Priority Data

May 29, 1987 [JP] Japan ................................ 62-131726

[51] Int. Cl.$^5$ ...................... C07K 15/12; C12N 15/19; C12N 15/03

[52] U.S. Cl. .................................... 530/351; 435/69.7; 435/320.1; 435/252.33; 536/27; 530/350

[58] Field of Search ............... 530/350, 387, 395, 351; 435/69.7, 320, 172.3, 252.33; 536/27

[56] References Cited

U.S. PATENT DOCUMENTS 4,617,266 10/1986 Fahnertock, Sr. .

4,920,196 4/1990 Aggarwal .......................... 530/351

FOREIGN PATENT DOCUMENTS

84/03103 8/1964 World Int. Prop. O. .

84/00773 3/1984 World Int. Prop. O. .

OTHER PUBLICATIONS

Wada et al., 1990, J. Biotechnology 13:325-334.

Olsner et al., 1982, Pharmac. Ther. 15:355-381.

Sjodahl et al., 1979, Scand. J. Immunol. 10:593-596.

Chemical Abstracts No. 107: 183548e of Hiroshi et al. JP 62,116,522, May 28, 1987.

Shetie et al., 1986, Molecular Immunology 23(12: 1373-1379.

Kim et al., 1988, Gene 68:315-321.

*Primary Examiner*—Garnette D. Draper
*Assistant Examiner*—Keith C. Furman
*Attorney, Agent, or Firm*—Wegner, Cantor, Mueller & Player

[57] ABSTRACT

A fused protein comprising a polypetide containing an antibody binding site of protein A and a polypeptide of lymphotoxin, and having biological activities of lymphotoxin and an ability to bind to an antibody is disclosed. Further, a process for the production of the fused protein, as well as a DNA coding for the fused protein, a plasmid containing the DNA, and *E. coli* transformed with the plasmid, necessary for the above-mentioned process, are provided.

9 Claims, 9 Drawing Sheets

Fig. 3-1

```
                 10              20              30              40              50              60
ATG CTC CCG GGT GTT GGT CTT ACT CCA TCA GCT GCC CAG ACT GCC CGT CAG CAC CCC AAG
Met Leu Pro Gly Val Gly Leu Thr Pro Ser Ala Ala Gln Thr Ala Arg Gln His Pro Lys
 0   1                                  10

                 70              80              90             100             110             120
ATG CAT CTT GCC CAC AGC AAC CTC AAA CCT GCT GCT CAC CTC ATT GGA GAC CCC AGC AAG
Met His Leu Ala His Ser Asn Leu Lys Pro Ala Ala His Leu Ile Gly Asp Pro Ser Lys
20                                      30

                130             140             150             160             170             180
CAG AAC TCA CTG CTC TGG AGA GCA AAC ACG GAC CGT GCC TTC CTC CAG GAT GGT TTC TCC
Gln Asn Ser Leu Leu Trp Arg Ala Asn Thr Asp Arg Ala Phe Leu Gln Asp Gly Phe Ser
40                                      50

                190             200             210             220             230             240
TTG AGC AAC AAT TCT CTC CTG GTC CCC ACC AGT GGC ATC TAC TTC GTC TAC TCC CAG GTG
Leu Ser Asn Asn Ser Leu Leu Val Pro Thr Ser Gly Ile Tyr Phe Val Tyr Ser Gln Val
60                                      70

                250             260             270             280             290             300
GTC TTC TCT GGG AAA GCC TAC TCT CCC AAG GCC ACC TCC TCC CCA CTC TAC CTG GCC CAT
Val Phe Ser Gly Lys Ala Tyr Ser Pro Lys Ala Thr Ser Ser Pro Leu Tyr Leu Ala His
80                                      90
```

Fig. 3-2

```
                310                 320                 330                     340                 350                 360
GAG GTC CAG CTC TTC TCC TCC CAG TAC CCC TTC CAT GTG CCT CTC CTC AGC TCC CAG AAG
Glu Val Gln Leu Phe Ser Ser Gln Tyr Pro Phe His Val Pro Leu Leu Ser Ser Gln Lys
100                                     110

                370                 380                 390                     400                 410                 420
ATG GTG TAT CCA GGG CTG CAG GAA CCC TGG CTG CAC TCG ATG TAC CAC GGG GCT GCG TTC
Met Val Tyr Pro Gly Leu Gln Glu Pro Trp Leu His Ser Met Tyr His Gly Ala Ala Phe
120                                     130

                430                 440                 450                     460                 470                 480
CAG CTC ACC CAG GGA GAC CAG CTA TCC ACC CAC ACA GAT GGC ATC CCC CAC CTA GTC CTC
Gln Leu Thr Gln Gly Asp Gln Leu Ser Thr His Thr Asp Gly Ile Pro His Leu Val Leu
140                                     150

                490                 500                 510
AGC CCT AGT ACT GTC TTC TTT GGA GCC TTC GCT CTG
Ser Pro Ser Thr Val Phe Phe Gly Ala Phe Ala Leu
160                                     170
```

Fig. 4-1

```
CTAAGGAGGTTGT ATG GAA CAA CGC ATA ACC CTG AAA GAA GCT TGG GAT CAA   46
              Met Glu Gln Arg Ile Thr Leu Lys Glu Ala Trp Asp Gln   13

CGC AAT GGT TTT ATC CAA AGC CTT AAA GAT GAT CCA AGC CAA AGT GCT AAC GTT TTA GGT  106
Arg Asn Gly Phe Ile Gln Ser Leu Lys Asp Asp Pro Ser Gln Ser Ala Asn Val Leu Gly   33

GAA GCT CAA AAA CTT AAT GAC TCT CAA GCT CCA AAA GCT GAT GCG CAA CAA AAT AAC TTC  166
Glu Ala Gln Lys Leu Asn Asp Ser Gln Ala Pro Lys Ala Asp Ala Gln Gln Asn Asn Phe   53

AAC AAA GAT CAA CAA AGC GCC TTC TAT GAA ATC TTG AAC ATG CCT AAC TTA AAC GAA GCG  226
Asn Lys Asp Gln Gln Ser Ala Phe Tyr Glu Ile Leu Asn Met Pro Asn Leu Asn Glu Ala   73

CAA CGT AAC GGC TTC ATT CAA AGT CTT AAA GAC GAC CCA AGC CAA AGC ACT AAC GTT TTA  286
Gln Arg Asn Gly Phe Ile Gln Ser Leu Lys Asp Asp Pro Ser Gln Ser Thr Asn Val Leu   93

GGT GAA GCT AAA AAA TTA AAC GAA TCT CAA GCA CCG AAA GCT GAT AAC AAT TTC AAC AAA  346
Gly Glu Ala Lys Lys Leu Asn Glu Ser Gln Ala Pro Lys Ala Asp Asn Asn Phe Asn Lys  113

GAA CAA CAA AAT GCT TTC TAT GAA ATC TTG AAT ATG CCT AAC TTA AAC GAA GAA CAA CGC  406
Glu Gln Gln Asn Ala Phe Tyr Glu Ile Leu Asn Met Pro Asn Leu Asn Glu Glu Gln Arg  133
```

Fig. 4-2

```
AAT GGT TTC ATC CAA AGC TTA AAA GAT GAC CCA AGC CAA AGT GCT AAC CTA TTG TCA GAA   466
Asn Gly Phe Ile Gln Ser Leu Lys Asp Asp Pro Ser Gln Ser Ala Asn Leu Leu Ser Glu   153

GCT AAA AAG TTA AAT GAA TCT CAA GCA CCG AAA GCG GAT AAC AAA TTC AAC AAA GAA CAA   526
Ala Lys Lys Leu Asn Glu Ser Gln Ala Pro Lys Ala Asp Asn Lys Phe Asn Lys Glu Gln   173

CAA AAT GCT TTC TAT GAA ATC TTA CAT TTA CCT AAC TTA AAC GAA GAA CAA CGC AAT GGT   586
Gln Asn Ala Phe Tyr Glu Ile Leu His Leu Pro Asn Leu Asn Glu Glu·Gln Arg Asn Gly   193

TTC ATC CAA AGC CTA AAA GAT GAC CCA AGC CAA AGC GCT AAC CTT TTA GCA GAA GCT AAA   646
Phe Ile Gln Ser Leu Lys Asp Asp Pro Ser Gln Ser Ala Asn Leu Leu Ala Glu Ala Lys   213

AAG CTA AAT GAT GCT CAA GCA CCA AAA GCT GAC AAC AAA TTC AAC AAA GAA CAA CAA AAT   706
Lys Leu Asn Asp Ala Gln Ala Pro Lys Ala Asp Asn Lys Phe Asn Lys Glu Gln Gln Asn   233

GCT TTC TAT GAA ATT TTA CAT TTA CCT AAC TTA ACT GAA GAA CAA CGT AAC GGC TTC ATC   766
Ala Phe Tyr Glu Ile Leu His Leu Pro Asn Leu Thr Glu Glu Aln Arg Asn Gly Phe Ile   253

CAA AGC CTT AAA GAC GAT CCG GGG|AAT TCC CGG GGA TCC GTC GAC CTG CAG               817
Gln Ser Leu Lys Asp Asp Pro Gly Asn Ser Arg Gly Ser Val Asp Leu Gln               270
```

Linker Region

Ligation Site

Fig. 7

```
      (261)                                                      (262)
Asp Pro Gly                                                      Asn Ser Arg Gly Ser Val ---
GAT CCG GGG        Sequence in Protein A-Coding Plasmid          AAT TCC CGG GGA TCC GTC ---
CTA GGC CCC TTA A                                                    GG GCC CCT AGG CAG ---
            EcoRI

Asn Ser Lys Gly Gly Leu Asn Met Leu Pro Gly Val Gly Leu Thr ---  Sequence in Lymphotoxin-coding
AAT TCA AAA GGA GGT TTA AAT ATG CTC CCG GGT GTT GGT CTT ACT ---  Plasmid
     GT TTT CCT CCA AAT TTA TAC GAG GGC CCA CAA CCA GAA TGA ---
EcoRI

Asp Pro Gly Asn Ser Lys Gly Gly Leu Asn Met Leu Pro Gly Val Gly Leu Thr ---  Sequence in Fused Protein-Coding
GAT CCG GGG AAT TCA AAA GGA GGT TTA AAT ATG CTC CCG GGT GTT GGT CTT ACT ---  Plasmid
CTA GGC CCC TTA AGT TTT CCT CCA AAT TTA TAC GAG GGC CCA CAA CCA GAA TGA ---
            EcoRI
```

FUSED PROTEIN COMPRISING LYMPHOTOXIN

TECHNICAL FIELD

The present invention relates to a fused protein comprising a polypeptide containing an antibody binding site of protein A and a polypeptide of lymphotoxin, DNA coding for the fused protein, plasmids containing the DNA, *Escherichia coli* transformed with the plasmid, and a process for production of the fused protein using the *E. coli.*

BACKGROUND ART

Recently, studies have been made of targeting therapy, wherein a monoclonal antibody specific to cancer cells is linked to a anticancer substance to focus the anticancer substance onto the cancer tissue using the specificity of the monoclonal antibody.

Although, as anticancer substances used in such an approach, a plant toxin ricin, diphtheria toxin and the like have been studied, the use of lymphotoxin as a anticancer substance for the targeting therapy has not been attempted.

As methods of linking a cancer-specific antibody and an anticancer substance wherein they are directly covalently linked, a method wherein a liposome encapsulating an anticancer substance is linked to a cancer-specific antibody, and the like, is known.

Nevertheless, an attempt wherein an affinity of protein A to an antibody is used to link a cancer-specific antibody and an anticancer substance for the targeting therapy has not been made.

Although it is already known to prepare a fused protein comprising protein A and a physiologically active peptide (WO 84/03103), this approach is mainly directed to an affinity purification of the physiologically active peptide and the preparation of an antigen for immunization.

A conventional approach wherein an anticancer substance is chemically linked to a cancer-specific antibody for the targeting therapy is disadvantageous in that it is difficult to make the anticancer substance enter cancer cells. Conversely, it is known that lymphotoxin selectively and directly kills cancer cells via receptors on a surface of the cancer cell. Accordingly, the present invention is intended to provide a means of an effective cancer therapy such as a targeting therapy using lymphotoxin having such an advantageous property.

DISCLOSURE OF THE INVENTION

To attain the above-mentioned object, the present invention provides a fused protein comprising a polypeptide containing an antibody binding site of protein A and a polypeptide of lymphotoxin, and having both a biological activity originally exhibited by the lymphotoxin, i.e., anticancer action, and an ability to bind to the antibody originally exhibited by protein A; as well as a process for production of the fused protein, and DNA coding for the fused protein necessary for that production process, plasmids containing the DNA and *E. coli* transformed with the plasmid.

BRIEF DESCRIPTION OF THE DRAWINGS

FIGS. 3-1 and 3-2 show a nucleotide sequence of DNA coding for a native lymphotoxin in a starting plasmid pLTM2 for the construction of plasmids of the present invention, and an amino acid sequence of a corresponding polypeptide;

FIGS. 4-1 and 4-2 show a part relating to the present invention of a nucleotide sequence of DNA coding for protein A in plasmid pRIT2T, and an amino acid sequence of a corresponding polypeptide;

BEST MODE OF CARRYING OUT THE INVENTION

Since the present fused protein exhibits an anticancer action at the lymphotoxin protein thereof and has an ability to bind to an antibody at the protein A portion thereof due to its affinity therewith, the fused protein can bond to an antibody specific to a cancer, for example, a monoclonal antibody, to form a complex. Therefore, when such a complex is parenterally administered, it is expected to concentrate at cancer cells, where the fused protein is given to the cancer cells by the affinity between lymphotoxin receptors on a surface of the cancer cell and the fused protein.

A. Fused protein and DNA codinc therefor

The present fused protein comprises a polypeptide containing an antibody binding site of protein A and a polypeptide of lymphotoxin, and optionally, containing an oligopeptide between these polypeptides.

Figure 1:
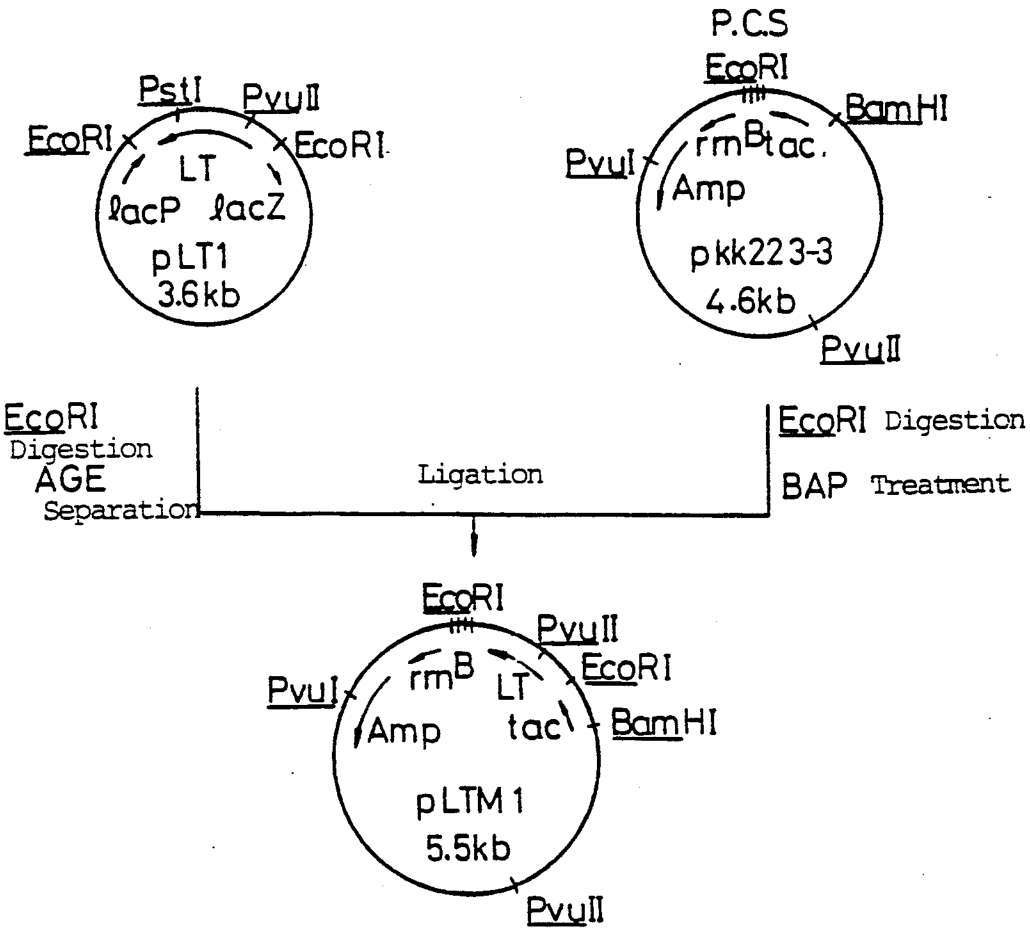
FIG. 1 shows the construction of plasmid pLTM1.
Figure 2:
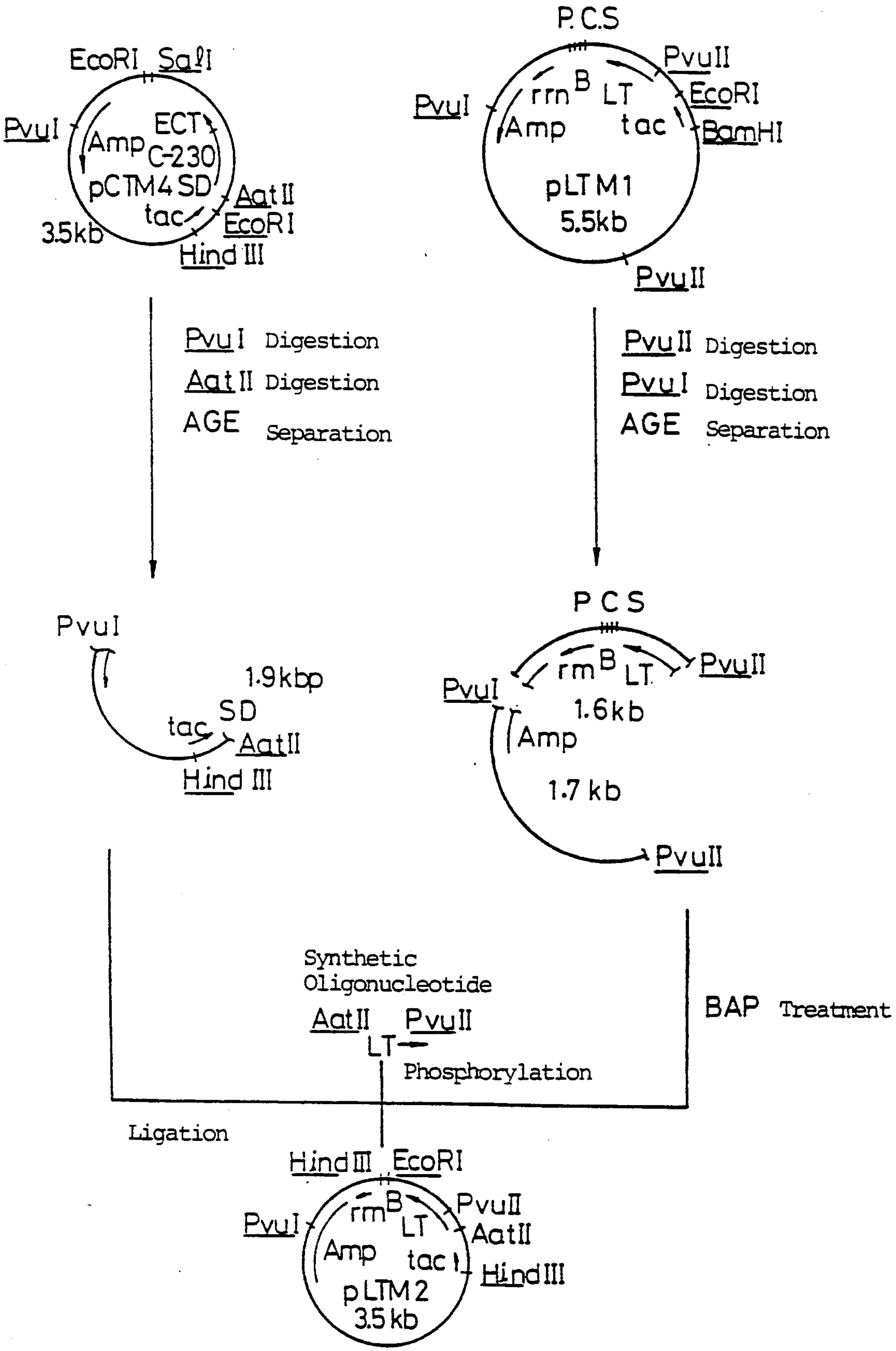
FIG. 2 shows the construction of plasmid pLTM2.
Figure 5:
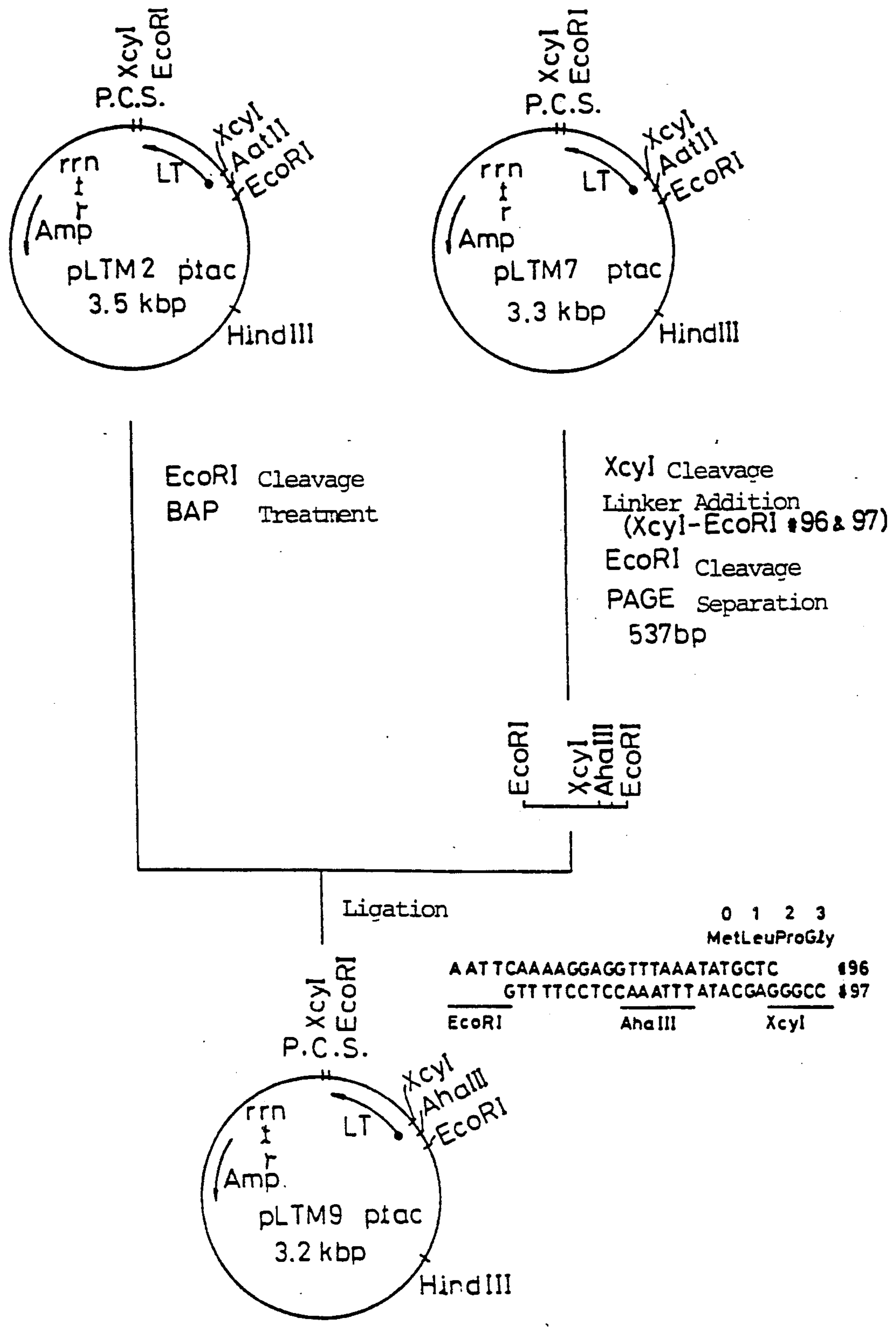
FIG. 5 shows the construction of plasmid pLTM9.

(1) Polypeptide containing an antibody binding site of protein A and DNA coding therefor The length of this protein is not critical as long as it possesses an antibody binding ability. An amino acid sequence of protein A has been already determined, and a plasmid containing a DNA coding the protein A is commercially available, and therefore, such a plasmid can be used in the present invention, as a starting plasmid. One of these plasmids, for example, plasmid pRIT2T, is available from Pharmacia (FIG. 5). In a nucleotide sequence coding for an amino acid sequence of protein A in this plasmid, a portion relating to the present invention is shown in FIGS. 4-1 and 4-2.

(2) Polypeptide of lymphotoxin and DNA coding therefor

A polypeptide of any length can be used as this portion, as long as it exhibits a biological activity of lymphotoxin in the form of a fused protein. As an embodiment of the present invention, a full length peptide of human lymphotoxin is used.

A series of plasmids pLT1, pLTM1, and pLTM2 containing a cDNA for native lymphotoxin have already been obtained, and the construction processes thereof are described in detail in Japanese Patent Application No. 61-123700. *Escherichia coli* X 1776/pLT1, which contains the plasmid pLT1, was deposited with the Fermentation Research Institute Agency of Industrial Science and Technology (FRI) as FERM P-8784, and *Escherichia coli* X 1776/pLTM2, which contains the plasmid pLTM2, was deposited with the FRI as FERM P-8785. The processes for the construction of these plasmids are described hereinafter in Reference Examples, and summarized in FIGS. 1 and 2. Accordingly, construction of the plasmids of the present invention can be started from the above-mentioned plasmids. Note, the DNA sequence coding for lymphotoxin in the starting plasmid of the present invention, and a corresponding amino acid sequence, are set forth in FIGS. 3-1 and 3-2.

(3) Linker oligonucleotide and DNA sequence coding therefor

In the present invention, an oligonucleotide sequence such as a consensus SD sequence is optionally inserted between a DNA coding for a polypeptide containing an antibody binding site of protein A and a DNA coding for a polypeptide of lymphotoxin, during the construction of an expression plasmid coding for the present fused protein. Therefore, the present fused protein includes, in addition to those wherein a polypeptide containing an antibody binding site of protein A is directly linked to a polypeptide of lymphotoxin, those wherein they are linked via an oligonucleotide linker encoded by the above-mentioned oligonucleotide.

B. Plasmid

The plasmids of the present invention are those containing the above-mentioned DNA coding region under the control of appropriate control sequences, and capable of expressing the DNA code sequence in *E. coli*. As a promoter, for example, a $P_L$ promoter, tac promoter, trp promoter, lacUV5 promoter or the like can be used, and as an SD sequence, for example, an SD sequence of a metapyrocatechase gene and a consensus SD sequence can be used.

To enhance the expression of lymphotoxin in *E. coli*, the present inventors constructed three plasmids, pLTM7, pLTM9, and pLTM11, from a plasmid pLTM2. In the plasmid pLTM7, the 3'-non-translation region of lymphotoxin in the plasmid pLTM2 has been deleted, and therefore, due to a lack of a region present in the deleted region, which destabilizes the mRNA, the expression level can be increased by about two times. The plasmid pLTM9 comprises the plasmid pLTM7 provided with an ideal consensus SD sequence, and due to the improvement of an SD region, the expression level is further increased by about two times. The plasmid pLTM11 is a plasmid wherein codons for leucine and proline following the N-terminal methionine in the plasmid pLTM9 have been improved in a manner which is preferable for the transcription of mRNA, and the expression level is increased by a further about two times.

(1) Construction process for plasmid pLTM7

A DNA fragment containing the lymphotoxin gene is obtained from the starting plasmid pLTM2 containing a lymphotoxin gene, using EcoRI, and inserted to M13 phage at the EcoRI site, and a specific nucleotide replacement mutagenesis is carried out using an oligonucleotide primer to insert an EcoRI site downstream of a translation stop codon of the lymphotoxin gene, to thus obtain a mutant phage LTM61.

A double-stranded DNA of the mutant phage is cut with EcoRI to obtain the lymphotoxin gene, which is then inserted to an EcoRI vector fragment of plasmid pLTM2 from which the lymphotoxin gene has been deleted, to obtain a plasmid pLTM7. This process is described in detail in Example 1.

(2) Construction process for plasmid pLTM9

Next, the plasmid pLTM7 is cleaved with a restriction enzyme XcyI to generate a DNA fragment containing the lymphotoxin gene, and the above-mentioned linker is attached to this fragment, and by an additional cleavage with EcoRI, an EcoRI-EcoRI DNA fragment of 537 bp comprising the lymphotoxin gene and the linker nucleotide is obtained. This DNA fragment is inserted to an EcoRI vector of the plasmid pLTM2 from which the lymphotoxin gene has been deleted, to obtain a plasmid pLTM9. The detailed process and sequence of an oligonucleotide used as a linker are set forth in Example 2.

(3) Construction process for plasmid pLTM11

A phage LTM18 and plasmid pLTM11 are obtained from the plasmid pLTM9, by a procedure similar to the construction process for the plasmid pLTM7. This process is described in detail in Example 3.

(4) Construction process for plasmid pPRALT1

The plasmid pLTM9 containing lymphotoxin gene is cut with EcoRI to obtain a DNA fragment containing lymphotoxin gene, which is then inserted to an EcoRI site of a plasmid pRIT2T coding for the above-mentioned protein A to obtain a plasmid pPRALT1 containing a gene coding for a fused protein of the present invention. This process is described in detail in Example 4. *Escherichia coli* X 1776/pPRALT1, which contain the above-mentioned plasmid pPRALT1, was deposited with the Fermentation Research Institute Agency of Industrial Science and Technology, 1-3, Higashi 1 chome Tsukuba-shi, Ibaraki-ken, 305, Japan, as FERM BP-1899 (original national deposition FERM P-9389).

C. *E. coli* to be transformed

According to the present invention, any strain of *E. coli* conventionally used for production of a polypeptide by a gene engineering technique can be used and, for example, N48301, RR1, RB791, SM32, HB101, N99, JM103 and the like are mentioned.

D. Expression of desired polypeptide

To express a desired protein, *E. coli* transformed with the above-mentioned plasmid is cultured in, for example, an LB medium by a conventional method, and an induction is applied in accordance with a promoter used. Next, the produced polypeptide is recovered from the cells of *E. coli* to obtain the desired polypeptide. This method is hereinafter described in detail in the Examples.

E. Cytotoxic activity

Cytotoxic activity of the polypeptide obtained as described above can be measured by, for example, a microplate method. This measuring method and the results obtained are described hereinafter in detail in the Examples.

The present fused protein maintains the cytocidal activity originally exhibited by lymphotoxin.

F. Affinity of fused protein to antibody

As described in detail in the Examples, the present fused protein has an affinity to an antibody, and can complex with the antibody.

The present invention is now more specifically described in the Examples.

EXAMPLE 1

Construction of Plasmid pLMTM7

(1) Introduction of EcoRI site to a position immediately downstream of a stop codon The plasmid pLTM2 was cleaved with the restriction enzyme EcoRI, and a fragment containing a lymphotoxin gene was recovered from 0.8% agarose.

Then, 0.5 pmole of this DNA fragment was mixed with 0.5 pmole of double-stranded DNA of phage M13mp10 which had been cleaved with EcoRI, and the mixture was ligated in 20 μl of a solution containing 66 mM Tris-HCl (pH 7.5), 5 mM $MgCl_2$, 5 mM DTT and 1 mM ATP using 100 units of T4 DNA ligase at 12° C. for 16 hours. After the reaction, the reaction mixture was used to transform *E. coli* JM103 by a procedure of Messing et al., Methods in Enzymology, 101, 20-78, 1983, and the mixture was plated with soft agar containing 0.02% X-gal and 1 mM IPTG, and cultured at 37° C. overnight. A single stranded template DNA was prepared from a white plaque formed by transformant. Namely, the white plaque was picked up with a toothpick, and suspended in 1.5 ml of 2XYT culture medium (1.6% Bacto trypton, 1% yeast extract and 0.5% NaCl) in which *E. coli* JM103 was growing, and culturing was carried out at 37° C. for five hours. A single-stranded recombinant phage DNA was recovered from the supernatant by polyethyleneglycol precipitation, phenol treatment, and ethanol precipitation.

The single-stranded DNA thus obtained was used as a template to determine a nucleotide sequence, by a dideoxy method of Messing et al., (supra) to confirm a sequence of the cloned single-stranded DNA. In this manner, a single-stranded DNA comprising an anti-coding strand of lymphotoxin gene was obtained, and this recombinant phage was designated as LTM21.

A single-stranded DNA of LTM21 thus obtained was used as a template, and a synthetic oligonucleotide:

CGC TCT GTA GAA TTC GGA AAA ATC CAG was used as a primer, to carry out a repair reaction using a Klenow fragment of DNA polymerase. Namely, 2 pmoles of the primer phosphorylated at the 5'-terminal thereof were added to 0.5 pmole of the single-stranded template DNA, and were maintained in 10 μl of a solution containing 7 mM Tris-HCl (pH 7.5), 0.1 mM EDTA, 20 mM NaCl and 7 mM $MgCl_2$ at 60° C. for 20 minutes, and then at 23° C. for 20 minutes. Next, dATP, dGTP, dTTP and dCTP were added to this mixture to a final concentration of 5 mM to make a total volume of 20 μl, 2 units of DNA polymerase were added thereto, and incubation was carried out at 23° C. for 20 minutes. Next, 1 μl of 10 mM ATP and one unit of T4 DNA ligase were added, and incubation was carried out overnight at 12° C.

The thus obtained 0.1 pmole of a double-stranded DNA was used to transform *E. coli* JM103 by the Messings method.

The phage plaques thus obtained were screened for mutant phage by plaque hybridization using the above-mentioned oligonucleotide (phosphorylated with $^{32}P$) as a probe. Namely, the plaques were transferred from the soft agar medium to a nitrocellulose filter, by a Benton—Davis method (W.D. Benton and R.W. Davis, Science, 196, 180,1977), and the filter was baked in vacuum at 80° C. for two hours. This nitrocellulose was subjected overnight to hybridization in 6X SSC, 10X Denhardt solution using the primer oligonucleotide labeled with $^{32}P$ as a probe at 23° C. Next, this filter was washed in 6X SSC at 59° C., and autoradiographed to isolate a mutant phage plaque exhibiting a positive signal.

A double-stranded phage was prepared by a rapid isolation method from this phage plaque and cleaved with EcoRI to obtain a 715 bp fragment, which was then used as a template for a determination of a nucleotide sequence by the dideoxy method, to confirm that a nucleotide replacement mutation had occurred and a phage having a EcoRI site immediately downstream of the stop codon of lymphotoxin gene was obtained. This mutant phage was designated as JM103/LTM61.

(2) Construction of plasmid and transformation

A double-stranded DNA was prepared from the phage JM103/LTM61 by a conventional procedure, and cleaved with a restriction enzyme EcoRI, and a DNA fragment containing a lymphotoxin gene was recovered by 0.8% agarose gel electrophoresis and purified by Elutip-d. Then 0.5 pmole of the above-mentioned DNA fragment was ligated with 0.5 pmole of an EcoRI fragment not containing a lymphotoxin gene of a plasmid pLTM2 in 40 mM HEPES (pH 7.8), 10 mM $MgCl_2$, 10 mM DTT, 0.4 mM ATP, using 100 units of T4 ligase, at 12° C. for 16 hours.

Subsequently, 10 μl of this reaction mixture was used to transform *E. coli* RRl, and a transformant resistant to 100 μg/ml ampicillin was selected. Plasmid DNA was extracted from a colony of the transformant, and the nucleotide sequence thereof was confirmed by the dideoxy method. This plasmid was designated as pLTM7.

EXAMPLE 2

Construction of Plasmid pLTM9 (FIG. 5)

First, 24 μg of the plasmid pLTM7 (156μl ) was incubated with 60 units of restriction enzyme XcyI (24 μl) and 20 μl of XcyI buffer at 37° C. for four hours, and then 9 μg (20μl ) each of 5'-phosphorylated oligonucleotides #96 and #97:

```
AATTCAAAAGGAGGTTTAAATATGCTC        #96
    GTTTTCCTCCAAATTTATACGAGGGCC    #97
EcoRI          Aha III       XcyI
```

were added to the reaction mixture, the mixture was extracted with phenol and chloroform, and DNA was precipitated with ethanol and dried. This DNA was reacted in 40 mM HEPES (pH 7.8), 10 mM $MgCl_2$, 10 mM DTT and 0.4 mM ATP, using 100 units of T4 ligase, at 12° C. for 16 hours. The reaction mixture was then extracted with phenol and chloroform, and subsequently, DNA was precipitated with ethanol and dried.

This precipitate was dissolved in 160 μl of distilled water, the solution was mixed with 300 units of EcoRI (20 μl ) and 20 μl of an EcoRI buffer, the mixture was incubated at 37° C. for two hours, and then frozen.

This reaction mixture was separated by electrophoresis using 2% agarose gel, and a gel section containing a 537 bp DNA fraction was cut out and subjected to an electrodialysis in a dialysis membrane. The extract was applied to an Elutip-d column, and after the DNA was adsorbed, the column was washed, and by increasing an ion concentration in an eluent, the DNA was eluted and recovered. The DNA was precipitated with ethanol, and the precipitated DNA was dried and dissolved in 20 μl of distilled water.

Then 0.5 pmole of EcoRI fragment not containing a lymphotoxin gene of plasmid pLTM2 was ligated with 0.5 pmole of the above-mentioned DNA fragment in 40 mM HEPES (pH 7.8), 10 mM $MgCl_2$, 10 mM DTT, 0.4 mM ATP, using 100 units of T4 ligase, at 12° C. for 16 hours.

Then 10 μl of this reaction mixture was used to transform *E. coli* RRl, and a transformant resistant to 100 μg/ml ampicillin was selected. Plasmid DNA was extracted from a colony of the transformant, and the nucleotide sequence thereof was confirmed by the dideoxy method. This plasmid was designated as pLTM9.

EXAMPLE 3

Construction of plasmid pLTM11

The plasmid pLTM9 having modified codons for the second leucine and the third proline was cleaved with restriction enzyme EcoRI, and a fragment containing the lymphotoxin gene was recovered from 0.8% agarose gel.

Then 0.5 pmole of this DNA fragment was mixed with 0.5 pmole of a double-stranded DNA of phage M13 mp10 which has been cleaved with EcoRI, and ligation was carried out in 20 μl of a solution containing 66 mM Tris-HCl (pH 7.5), 5 mM $MgCl_2$, 5 mM DTT and 1 mM ATP, using 100 units of T4 DNA ligase, at 12° C. for 16 hours. After the reaction, the reaction mixture was used to transform *E. coli* JM103 by the Messing et al., Method in Enzymology, 101, 20–78, 1983, and the mixture was plated with soft agar containing 0.02% X-gal and 1 mM IPTG, and culturing was carried out overnight at 37° C. From a white plaque formed by a transformant, a single-stranded DNA was prepared. Namely, a white plaque was picked up with a toothpick, suspended in 1.5 ml of 2X YT medium (1.6% Bacto trypton, 1% yeast extract and 0.5% NaCl) in which *E. coli* JM103 was growing, and culturing was carried out at 37° C. for five hours to obtain a culture supernatant from which a single-stranded recombinant phage DNA was recovered by polyethyleneglycol precipitation, phenol treatment, and ethanol precipitation.

The nucleotide sequence of the single-stranded DNA thus obtained was determined by the dideoxy method of Messing et al., supra, and a sequence of cloned single-stranded DNA was confirmed. In this way, a single-stranded DNA containing an anti-coding strand of the lymphotoxin gene was obtained. This recombinant phage was designated as LTM71.

A single-stranded DNA of the LTM71 thus obtained was used as a template with a synthetic oligonucleotide:

T TTA AAT ATG TTA CCT GGT GTT GG as a primer to carry out a repair reaction using a Klenow fragment of DNA polymerase. Namely, 2 pmoles of the primer phosphorylated at the 5'-terminal thereof were added to 0.5 pmole of the single-stranded template DNA, and were maintained in 10 μl of a solution containing 7 mM Tris-HCl (pH 7.5), 0.1 mM EDTA, 20 mM NaCl and 7 mM $MgCl_2$ at 60° C. for 20 minutes, and then at 23° C. for 20 minutes. Next, dATP, dGTP, dTTP and dCTP were added to this mixture to a final concentration of 5 mM to make a total volume of 20 μl, 2 units of DNA polymeran were added thereto, and incubation was carried out at 23° C. for 20 minutes. Next, 1 μl of 10 mM ATP and one unit of T4 DNA were added, and incubation was carried out overnight at 12° C.

Then 0.1 pmole of a double-stranded DNA thus obtained was used to transform *E. coli* JM103 by the Messing method.

The phage plaques thus obtained were screened for mutant phage by plaque hybridization using the above-mentioned oligonucleotide (phosphorylated with $^{32}P$) as a probe. Namely, the plaques were transferred from the soft agar medium to a nitrocellulose filter by a Benton —Davis method (W.D. Benton and R.W. Davis, Science, 196, 180, 1977), and the filter was baked in a vacuum at 80° C. for two hours. This nitrocellulose was subjected overnight to hybridization in a 6X SSC, 10X Denhardt solution using the primer oligonucleotide labeled with $^{32}P$ as a probe at 23° C. Next, this filter was washed in 6X SSC at 59° C., and autoradiographed to isolate a mutant phage plague exhibiting a positive signal.

A double-stranded phage was prepared from this phage plaque, by a rapid isolation method, and cleaved with EcoRI to obtain a 537 bp fragment, which was then used as a template for a determination of the nucleotide sequence in the dideoxy method to confirm that a nucleotide replacement mutation had occurred and codons for the second leucine and the third proline of the lymphotoxin gene were modified. This mutant phage was designated as JM103/LTM81.

A double-stranded DNA was prepared from the phage JM103/LTM81 by a conventional procedure, and cleaved with a restriction enzyme EcoRI, and a DNA fragment containing a lymphotoxin gene was recovered by 0.8% agarose gel electrophoresis and purified by Elutip-d.

Then 0.5 pmole of the above-mentioned DNA fragment was ligated with 0.5 pmole of an EcoRI fragment not containing a lymphotoxin gene of plasmid pLTM2 in 40 mM HEPES (pH 7.8), 10 mM MgCl , 10 mM DTT, 0.4 mM ATP, using 100 units of T4 ligase, at 12° C. for 16 hours.

Subsequently, 10 μl of this reaction mixture was used to transform *E. coli* RRl, and a transformant resistant to 100 μg/ml ampicillin was selected. A plasmid DNA was extracted from a colony of the transformant, and the nucleotide sequence thereof was confirmed by the dideoxy method. This plasmid was designated as pLTM11.

EXAMPLE 4

Figure 6:
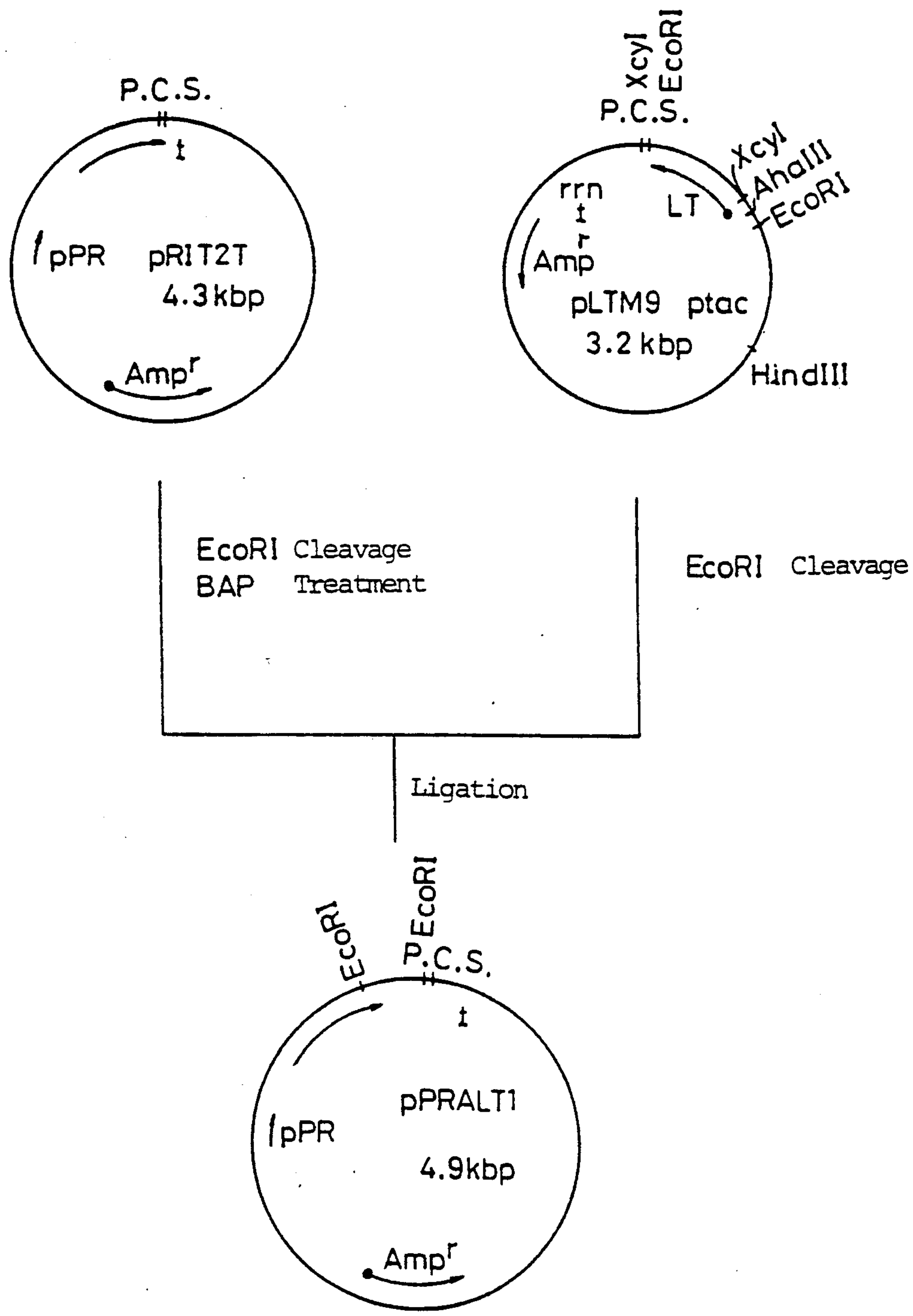
FIG. 6 shows the construction of plasmid pPRALT1 of the present invention; and, FIG. 7 shows a nucleotide sequence at a junction of the present fused protein and a corresponding amino acid sequence.

Construction of clasmid pPRALT1 (FIG. 6)

First, 5 μg of plasmid pRIT2T (obtained from Pharmacia (1μl ) was digested with 15 units of EcoRI (1μl ) at 37° C. for 5 hours, 40 μl of 20 mM Tris-HCl (pH 8.0) and 10μl of alkaline phosphatase (*E. coli* C75) (1/10 dilution) were added to the reaction mixture, and the reaction was carried out at 65° C. for 40 minutes.

The reaction mixture was extracted with phenol and chloroform, and DNA was recovered by ethanol precipitation, and dried.

Then 0.5 pmole of the DNA precipitate and 0.5 pmole of EcoRI fragment of the plasmid pLTM9 containing lymphotoxin gene were reacted in 40 mM HEPES (pH 7.8), 10 mM $MgCl_2$, 10 mM DTT and 0.4 mM ATP, using 100 units of $T_4$ ligase, at 12° C. for 16 hours.

Subsequently, 10 μl of this reaction mixture was used to transform *E. coli* RRl, and a transformant resistant to 100 μg/ml ampicillin was selected. Then plasmid DNA was extracted from a colony of the transformant, and the nucleotide sequence thereof was confirmed by the dideoxy method. This plasmid was designated as pPRALT1.

EXAMPLE 5

Confirmation of expression product by in vitro translation

Expression products obtained by in vitro translation of the present plasmid pPRALT1 coding for a fused protein comprising lymphotoxin and protein A and of plasmid pRIT2T coding for protein A were tested using a DNA expression kit (Amersham). The expression product was separated by SDS-PAGE using 10%-26% gradient, and apparent molecular weight was obtained by comparing the position of a band of the expression product and the position of bands of molecular weight standards. As a result, it was found that an expression product of pPRALT1 had a molecular weight of about 48K, and an expression product of pPIT2T had a molecular weight of about 30K, and therefore, it was confirmed that the plasmid pPRALT1 expressed a fused protein of the present invention.

EXAMPLE 6

Expression of polypeptide and purification

*E. coli* HB101 containing the above-mentioned plasmid pPRALT1 was incubated overnight in 30 ml of LB medium at 37° C., inoculated to 3 l of LB medium, and the culturing was carried out in a jar fermenter (Iwashiya) at 37° C. for 7 hours. After the culturing, the culture broth was centrifuged to collect microbial cells. The collected cells were thoroughly suspended in phosphate buffer (10 mM sodium phosphate, pH 7.2, 1 mM EDTA), and the suspension was passed three times through a Gaulin Homogenizer at 8000 psi to disrupt the cells. The disruptant was centrifuged at 10,000 rpm for 30 minutes to obtain a supernatant.

To this supernatant was added ammonium sulfate to 5% (w/v) to carry out ammonium sulfate precipitation, and a resulting supernatant was purified by a butyl Toyopearl column (Toso). Namely, 20 ml of the supernatant was applied to 20 ml of butyl Toyopearl 650 M which has been equilibrated with phosphate buffer (10 mM sodium phosphate, pH 7.2, 0.02% Tween 20) containing 5% (w/v) ammonium sulfate, and the column was immediately washed with 100 ml of the same buffer as used for equilibrating the column, and protein adsorbed to the column was eluted with phosphate buffer not containing ammonium phosphate. The eluted fraction contained the desired polypeptide.

EXAMPLE 7

Confirmation of antibody binding ability of desired polypeptide

It was confirmed that the desired polypeptide binds to an antibody and that the binding relied on the affinity of the protein A portion. Namely, the desired polypeptide obtained in Example 6 was subjected to SDS-PAGE, and transferred to a nitrocellulose membrane using a electroblotting apparatus (Biometra). After blocking the membrane with phosphate buffer containing 1% BSA, the membrane was treated with a peroxidase-labeled bovine anti-rabbit IgG (Bethyl Laboratory), and after washing 4-chloro-1-naphthol solution and an aqueous hydrogen peroxide were used to develop a color. As a result, a band of a dark violet was found at a position corresponding to a molecular weight of 44,000. The desired polypeptide bound to a peroxidase-labeled bovine antibody.

Cell extracts (supernatants) obtained from *E. coli* N48301 containing plasmid pPRALT1 and *E. coli* RR1 containing plasmid pLTM7 according to a procedure of Example 2 were diluted with phosphate buffer to $1 \times 10^4$ U/ml, and a culture supernatant from HUT-102 cells was diluted with phosphate buffer to $1 \times 10^3$ U/ml. To 300 μl of the solution was added 10μl of a column carrier, IgG Sepharose 6 fast flow (Pharmacia), and the whole was gently shaken at a room temperature for one hours. The mixture was centrifuged at 6000 rpm to obtain a supernatant A, and the precipitated carrier was washed three times with 200 μl each of phosphate buffer. After the carrier was separated from the washing solution by centrifugation at 6000 rpm, 300 μl of phosphate buffer containing 1 mg/ml protein A (Sigma) was added to the carrier, and the whole was gently shaken at a room temperature for one hour. The mixture was centrifuged at 6000 rpm to obtain a supernatant B.

Lymphotoxin activity of the supernatants A and B thus obtained was measured by the above-mentioned procedures, and the following result was obtained.

| Plasmid/*E. coli* | Supernatant A | Supernatant B |
|---|---|---|
| pPRALT1/N48301 | $1 \times 10^2$ | $6 \times 10^2$ |
| pLTM7/RR1 | $1 \times 10^3$ | 2 |
| HUT-102 Supernatant | $1 \times 10^2$ | 0 |
| Distilled water | 0 | 0 |

From the above-mentioned result, it was found that a product from *E. coli* containing the present plasmid pPRALT1, i.e., the supernatant B from an extract containing a fused protein comprising lymphotoxin and protein A exhibits lymphotoxin activity. This means that the fused protein was adsorbed to the carrier via an antibody (IgG) immobilized to the carrier, and then eluted by exchange with the added protein A.

Accordingly, it was proved by this experiment that the present polypeptide which is a fused protein comprising protein A and lymphotoxin can form a complex with an antibody.

EXAMPLE 8

Cytocidal activity

Cytocidal activity of the desired polypeptide was measured by a method of B.B. Aggarwal, J. Biological Chemistry, 260, 2345-2354. Mouse L-M cells were cultured in Eagle's MEM containing 5% fetal calf serum, 0.5% penicillin, 0.5% streptomycin and 1 μg/ml actinomycin D, and $3 \times 10^4$ cells/100 μl were put into a well of a plate in which 100 μl of the above-mentioned diluted sample was added, and culturing was carried out at 37° C. under an atmosphere of 5% $CO_2$ for 24 hours. After washing the plate, to which 100 μl of a formalinethanol solution containing 0.05% crystal violet was added to stain cells for 30 minutes. Next, the dyestuff was eluted with 100 μl of 0.05M NaH in ethanol, and absorbance at 570 nm was measured using a photometer (Minireader II, Dynatech).

The absorbance (normal scale) and dilution ratio (logarithmic scale) were plotted on a semilogarithmic coordinates, and the cytocidal activity in a sample, expressed in unit, was calculated defining an activity necessary to kill 50% of cells as one unit. The value of the cytocidal activity was corrected using TNF (Gene zyme) as an internal standard.

A cytocidal activity of the desired polypeptide obtained in Example 6 was $8.8\times10^5$ units per 1 mg protein. Accordingly, the present fused protein expressed by plasmid pPRALT1 has lymphotoxin activity.

Reference Example 1.

Preparation and screening of cDNA (1) Preparation of mRNA

Human T lymphatic leukemia cell line HUT-102 was suspended in 20 ml of RPMI-1640 medium containing 5% fetal calf serum, and cultured in a 5% $CO_2$ incubator at 37° C. for two to three days. A volume of the medium was then increased two-fold every two or three days during the culture, to finally obtain 1 l of the culture broth. The culture broth thus obtained was centrifugated at 4° C. and 3000 rpm for 10 minutes to collect the cells which were then suspended in 50 ml of a phosphate buffer (10 mM sodium phosphat, pH 7.2, 0.15 M NaCl) to wash the cells, and the suspension was centrifuged to obtain a pellet of T cells.

mRNA was prepared using the guanidinium/CsCl method of Maniatis et al., Molecular Cloning, Cold Spring Harbor Laboratory, p. 196, 1982. Namely, the T cell pellet was suspended in five volumes of guanidium isothiocyanate solution (6M guanidium isothiocyatate, 5 mM sodium citrate, pH 7.0, 0.1 M β-mercaptoethanol and 5% sarcosine), and the suspension was put into a glass homogenizer and homogenized ten times with a Teflon bar. The homogenate was carefully overlaid on 1.5 ml of solution (pH 7.5) containing 5.7M CsCl and 0.1M EDTA in a centrifuge tube (Ultra Clean, trade mark) for SW55 roter, and ultra centrifugation was carried out at 15° C. and 35,000 for 20 hours. Guanidium solution was removed, a wall of the tube was three times washed with the guanidium solution, the wall of the tube was cut at a level over a surface of CsCl solution. After the CsCl solution was removed, the precipitate was washed two times with 80% ethanol, and dissolved in 500 μl of a buffer containing 10 mM Tris-HCl (pH 7.4), 5 mM EDTA and 10% SDD (TES). The solution was extracted with 500 μl of chloroform/n-buthanol (4:1) mixture, and after an organic layer was extracted again with 500 μl of TES, aqueous layers were combined, and ethanol precipitation was carried out to obtain mRNA.

The mRNA was passed through an oligo (dT) cellulose column by a procedure described in Molecular Cloning, to purify poly (A)+RNA.

(2) Synthesis of cDNA

First, a strand of a cDNA was synthesized by a Gubler-Hoffman method. Namely, 8.4 μl of water, 1μl of 1M Tris-HCl (pH 8.3) (50 mM), 1μl of 0.6M KCl (30 mM), 1μl of 0.16M $MgCl_2$ (8 mM), 1μl of 20 mM DTT (1 mM), 1.6μl of 25 mM dNTP (mixture of 25 mM each dATP, dCTP, dGTP and dTTP) (each 2 mM), 1μl of RNasin (Biotech 30 V/μl), 2μl of oligo (dT) 12–18 (PL) (2μl ), and 3μl of HUT-102 poly(A)+ RNA (1μg/μl ) were mixed to make a total volume of 19μl, and after preincubation of 37° C. for 5 minutes, 1μl of reverse transcriptase (Life Science, 12.5 V/μl ) was added to the mixture, and reaction was carried out at 37° C. for one hour. Note, the values in parentheses represent final concentrations of the salts in the solution. After the reaction was terminated by addition of 1μl of 0.5M EDTA and 0.5μl of 10% SDS, phenol/-chloroform extraction, ammonium acetate/ethanol precipitation two times, and washing of the precipitate with 80% ethanol were carried out. the precipitate was dried under a reduced pressure, and dissolved in 50 μl of water. To 5 μl of the solution was added 1 μg of RNase, and the mixture was allowed to stand at a room temperature for 10 minutes and extracted with phenol. A resulting aqueous layer was subjected to 0.7% agarose gel electrophoresis to test an extent of elongation of the first strand.

A second strand was also synthesized according to a condition for synthesis of a second strand in the above-mentioned Gubler-Hoffman method. Namely, 45 μl of the cDNA first strand solution, 33.5 μl of water, 2μl of 1M Tris-HCl (pH 7.5) (20 mM), 1 μl of 0.5M $MgC_2$ (5 mM), 1 μl of 1M $(NH_4)_2$ (10 mM), 10 μl of 1M KCl (100 mM), 1 μl of 10 mM β-AND (0.1 mM); 1 μl of 5 mg/ml BSA (50 μg/ml), 1 μl of 4 mM NTP (40 μM), 1 μl of *E. coli* DNA ligase (PL, 0.5 μg/μl), 2 μl of *E. coli* DNA polymerase I (PL, 15 V/μl), 0.5 μl of *E. coli* RNase H (Takara Shuzo, 1.3 V/μl) and 1 μl of $^{32}$P-dCTP (10 μl) were mixed to make a total volume of 100 μl, and a reaction was carried out at 12° C. for one hour, and then at 22° C. for one hour. Before and after the reaction, 1 μl each of a sample was taken and an amount of incorporation of radioactivity was measured by TCA precipitation. After the reaction was terminated by an addition of 4 μl of 0.5M EDTA and 5 μl of 10% SDS to the reaction mixture, phenol/chloroform extraction, ethanol precipitation two times, and washing of the precipitate with 80% ethanol were carried out, and the precipitate was dried under a reduced pressure and dissolved in 10 μl of water.

(3) Preparation of cDNA library

Then 10 μl of cDNA aqueous solution, 2 μl of water, 0.7 μl of 1M Tris-acetate (pH 7.9) (35 mM), 1.3 μl of 1M potassium acetate (65 mM), 2 μl of 0.1M Magnesium acetate (10 mM), 1 μl of 10 mM DTT (1 mM) 1 μl of 5 mg/ml BSA (250 μg/ml), 1 μl of 2 mM dNTP (0.1 mM) and 1 μl of T4 DNA polymerase (Takara Shuzo, 1.5 V/μl ) were mixed to make a total volume 20 , 11 and reacted with 37° C. for 10 minutes. After the reaction was terminated by an addition of 1 μl of 0.5M EDTA and 0.5 μl of 10% SDS, phenol/chloroform extraction, ethanol precipitation two times, and washing the precipitate with 80% ethanol were carried out, and the precipitate was dried under a reduced pressure and dissolved in 10 μl of water.

To 2 μl of EcoRI linker (Takara Shuzo; GGAATTCC; 1 μg/μl ), were added 5 μl of water, 2 μl of 5X linker kinase buffer (0.33M Tris-HCl, pH 7.6, 5 mM ATP, 5 mM spermidine, 50 mM MgC12 , 75 mM DTT, 1 mg/ml BSA) and 1 μl of T4 DNA kinase (Takara Shuzo; 6 V/μl ) to make a total volume of 10 μl, and a reaction was carried out at 37° C. for one hour. To this reaction mixture were added 5 μl of a solution of cDNA previously blunt-ended as described above, 2 μl of 5X linker kinase buffer, 1.5 μl of water, 1 μl of T4 DNA ligase (Takara Shuzo; 175 V/μl), and 0.5 μl of T4 RNA ligase (PL; 0.8 μl ) to make a total volume of 20 μl, and a reaction was carried out at 12° C. overnight or at 22° C. for 6 hours. The reaction mixture was heated at 65° C. for 10 minutes to inactivate the ligases, and to the reaction mixture were added 65 μl of water, 10 μl of 10X EcoRI buffer and 5 μl of EcoRI (Takara Shuzo; 7.5 V/μl) to make a total volume of 100 μl. The reaction was carried out at 37° C. for 3 hours. One tenth volume each of samples were taken before and after the digestion with EcoRI, and subjected to 10% polyacrylamide gel electrophoresis to check whether the EcoRI linker was attached and whether the EcoRI site was cleaved. The reaction mixture was extracted with phenol, and after 5M NaCl was added to a resulting aqueous phase to a final concentration of 0.3M NaCl, the mixture was applied to a Sepharose CL-4B column (2 ml) to eliminate the EcoRI linker. The column was developed with TE (pH 7.6) and 0.3M NaCl, and 4 to 5 drops of fraction of the elute were obtained Fractions exhibiting radioactivity were then subjected to ethanol precipitation, and each precipitated fraction was dissolved in 10 μl of water.

A plasmid pUC9 was cleaved with EcoRI by a conventional procedure and treated with calf intestine alkaline phosphatase (CIP), mixed with 1 μl of the preparation (0.4 μg), 10 μl of the cDNA prepared as above, 20 μl of 5X linker kinase buffer and 64 μl of water, and the mixture heated at 68° C. for 10 minutes. To the mixture was added 5 μl of T4 DNA ligase to make a total volume of 100 μl, and the reaction was carried out at 12° C. overnight. The reaction mixture was heated at 65° C. for 10 minutes, and 10 μl of the reaction mixture was mixed with 210 μl of suspension of E. coli X 1776 competent cells to transform the cells. The transformed cell suspension thus prepared was added to 300 ml of X 1776 medium containing 50 μg/ml ampicillin, and cultured overnight at 37° C. A portion of the culture in the form of a 15% glycerine suspension was frozen at −80° C. and stored.

(4) Screening of cDNA library

First, 20 μl of the frozen glycerine storing suspension of the cDNA-containing transformants was diluted 5,000-fold with X 1776 medium and 100 μl of the diluted suspension was spread on a nitrocellulose sheet placed on an X 1776 agar plate containing ampicillin, and cultured overnight at 37° C. Colonies developed on the nitrocellulose sheet were replicated to two nitrocellulose sheets, and these replicas were cultured on X 1776 medium for three hours. The sheets were transferred onto the medium containing 10 μg/ml chlorophenical, followed by culturing overnight. The filter was subsequently put on 10% SDS, a denaturation solution (0.5N NaOH, 1.5M NaCl), and on a neutralizing solution (1.5M NaCl, 0.5M Tris-HCl, pH 8.0) each for 5 minutes The sheet was reacted in 5 μl of a proteinase K solution 1 mg/ml proteinase K (Merk], 0.5M NaCl, 10 mM Tris-HCl (pH 7.5), 5 mM EDTA, 0.1% SDS) at 37° C. for one hour, put between filter papers, strongly rubbed with a roller, twice washed with 2X SSC, and heated at 80° C. for three hours.

The above-mentioned nitrocellulose sheet was hybridized overnight with oligonucleotide probe #71 labeled with $^{32}P$ in 6X SSC, 10X Denhardt solution at 42° C. Next, the sheet was washed at 55° C. in 6X SSC, subjected to autoradiography for two days, and as a result, three colonies exhibited positive signals.

Next, this nitrocellulose sheet was washed in 1X SSC solutions at 65° C. for 30 minutes, to wash the positive signal away, dried, and again subjected to hybridization with the oligonucleotide probe #72. The hybridization was carried out overnight in 6X SSC, 10X Denhardt solution with the oligonucleotide probe #72 labeled with $^{32}P$ at 42° C. Next, this sheet was washed in 6X SSC at 50° C., and subjected to autoradiography for two days, and as a result, the same three colonies as those which exhibited a positive signal with the probe #71 again exhibited a positive signal.

Plasmid DNA was extracted from each of these three colonies, and the nucleotide sequence thereof was determined by a conventional procedure. As a result, one of these clones contained a coding sequence for an entire lymphotoxin peptide. This plasmid was designated as pLTl (FIG. 1).

REFERENCE EXAMPLE 2

Construction of plasmid pLMTl (FIG. 1)

The above-mentioned plasmid pLMT1 was used to transform *E. coli* RRl, the transformant was cultured, and plasmid DNA was extracted from the cultured cells.

Then 40 μl (20 μg) of pLT1 plasmid DNA, 20 μl of EcoRI buffer (X10), 140 μl of distilled water and 4 μl of EcoRI enzyme solution (40 units) were mixed, and reacted at 37° C. for three hours. This reaction mixture was extracted with 100 μl each of phenol and chloroform, washed with 200 μl of ether, and the DNA was precipitated with ethanol. After drying, the precipitate was dissolved in 100 μl of an electrophoresis dye solution, and separated by electrophoresis with 1.2% agarose gel in 1X TBE (Tris-Borate-EDTA buffer), and a gel piece containing a desired DNA of about 0.9 kb was cut off. This gel piece was put into a dialysis tube, and subjected to electroelution in lX TBE for two hours. The solution in the dialysis tube was recovered and applied on an Elutip-d column to adsorb the DNA on the column, which was then washed, and the DNA was eluted, by increasing an ion concentration of an eluent, and recovered. After ethanol precipitation, the precipitate was dried for three minutes, and the DNA thus obtained was dissolved in 20 μl of distilled water.

Subsequently, 10 μl of plasmid pKK223-3-containing solution, 5 μl of EcoRI buffer (X10), 36 μl of distilled water and 3 μl of EcoRI (30 units) were mixed, and reacted with 37° C. for three hours. Next, to this reaction mixture were added 50 μl of 50 mM Tris-HCl (pH 8.0) and 10 μl of bacterial alkaline phosphatase (BAP) C-75 solution (1/10 dilution), and a reaction was carried out at 65° C. for one hour. The reaction mixture was extracted with 100 μl each of phenol and chloroform, washed with 200 μl of ether and ethanol-precipitated, and the precipitate was dried for three minutes and dissolved in 20 μl of distilled water.

5 μl of the above-mentioned pKK223-3 digest, 5 μl of the above-mentioned pLTl digest, 10 μl of 100 mM HEPES (pH 7.8), 10 μl of 30 mM MgCl , 1 μl of 300 mM DTT, 1 μl of 10 mM ATP and 2 μl of T4 DNA ligase solution (20 units) were mixed, and reacted overnight at 12° C.

Then, 10 μl of this reaction mixture and 200 μl of a suspension of *E. coli* JM103 competent cells were mixed, and the mixture was spread on an H plate, and culturing was carried out overnight at 37° C. Among the many colonies formed, 12 colonies were analyzed by a rapid isolation method, and it was confirmed that three colonies contained a desired plasmid. This plasmid was designated as pLTM1.

REFERENCE EXAMPLE 3

Construction of plasmid pLTM2 (FIG. 2)

First, 100 μl (10 μg) of plasmid pLTM1 solution, 40 μl of Pvu II buffer (X10), 260 μl of distilled water and 4 μl of Pvu II enzyme buffer (40 units) were mixed, and reacted at 37° C. for one day. To this reaction mixture were added 360 μl of distilled water, 40 μl of Pvu I buffer and 4 μl of Pvu I enzyme solution (40 units), and a reaction was carried out for one day at 37° C. The reaction mixture was extracted with 400 μl each of phenol and chloroform, washed with 800 μl ether, and ethanol-precipitated. The precipitate was dried, and dissolved in 100 μl of a dye solution for agarose gel electrophoresis, and subjected to electrophoresis with 1.2% agarose gel in lX TBE. Gel piece containing DNA having lengths of about 1.6 kb and 1.7 kb was cut off. This gel piece was put into a dialysis tube, and electroelution was carried out in lX TBE for two hours, and the solution in the dialysis tube was recovered and applied to an Elutip-d column to absorb DNA to the column. After washing the column, the DNA was eluted, by increasing a concentration of an eluent, and recovered. The DNA was precipitated with ethanol, and the precipitate was dried for three minutes and dissolved in 20 μl of distilled water. To this solution, were added 380 μl of lM Tris-HCl (pH 8.0) and 4 μl of BAP C-75 enzyme solution (1/10 dilution), and a reaction was carried out for one hour at 65° C. This reaction mixture was extracted with 300 μl each of phenol and chloroform, and washed with 600 μl of ether.

*E. coli* JM103 containing plasmid pCTM4 was cultured by a conventional procedure, and plasmid DNA was extracted from the cultured cells by a conventional procedure. DNA was precipitated with ethanol, and the precipitate was dried for three minutes and dissolved in 400 μl of distilled water. This solution was extracted with 300 μl each of phenol and chloroform, and washed with 600 μl of ether.

Then 100 μl of the above-mentioned solution containing DNAs of about 1.6 kb and 1.7 kb, 50 μl of the above-mentioned solution containing DNA of about 1.9 kb, 20 μl (75 μg) each of 5'-phosphorylated oligonucleotides #73 and #74:

```
   CATGCTCCCGGGTGTTGGTCTTACTCCATCAG   #73
TGCAGTACGAGGGCCCACAACCAGAATGAGGTAGTC  #74
```

10 μg of tRNA and 50 μl of 3M sodium phosphate were mixed, and to the mixture was added 1 ml of ethanol, and the mixture allowed to stand for 20 minutes at −80° C., and centrifuged for ten minutes at 4° C. and 16000 rpm to coprecipitate the DNAs with the tRNA. After removing a supernatant, the precipitate was dried and dissolved in a mixture of 8 μl of 30 mM MgC12 , 4 μl of distilled water, and 100 mM HEPES (pH 7.5), and annealing was carried out at 65° C. for 20 minutes, at 42° C. for 30 minutes, at a room temperature for five minutes, and then for five minutes on ice. To this mixture were added 1 μl of 10 mM ATP, 1 μl of 300 mM DTT, 9 μl of 40% PEG and 2 μl of T4 DNA ligase solution (20 minutes), and a reaction was carried out overnight at 20° C.

Then 10 μl of this ligation mixture was used to transform *E. coli* RRl by the Hunahan method, and the transformation mixture was spread on an LB ampicillin plate, and culturing was carried out overnight at 37° C. As a result, 55 colonies developed, and among them, 9 colonies were analyzed by a rapid isolation method, and was confirmed that two colonies contains the desired plasmid. This plasmid was designated as pLTM2.

This plasmid was used to transform *E. coli* JM103 and X 1776 to obtain *Escherichia coli* JM103/pLTM2, and *Escherichia coli* X 1776/pLTM2.

We claim:

1. A fused protein comprising a polypeptide containing a antibody binding site of protein A and a polypeptide of lymphotoxin, and having anti-cancer action of lymphotoxin and an ability to bind to the Fc domain of an antibody.

2. A fusion protein according to claim 1, wherein the polypeptide containing an antibody binding site of protein A is linked with the polypeptide of lymphotoxin directly or via a linker peptide.

3. A fusion protein according to claim 2 having the following amino acid sequence:

Met Glu Gln Arg Ile Thr Leu lys Glu Ala Trp Asp Gln Arg Asn
Gly Phe Ile Gln Ser Leu Lys Asp Asp Pro Ser Gln Ser Ala Asn
Val Leu Gly Glu Ala Gln Lys Leu Asn Asp Ser Gln Ala Pro Lys
Ala Asp Ala Gln Gln Asn Asn Phe Asn Lys Asp Gln Gln Ser Ala
Phe Tyr Glu Ile Leu Asn Met Pro Asn Leu Asn Glu Ala Gln Arg
Asn Gly Phe Ile Gln Ser Leu Lys Asp Asp Pro Ser Gln Ser Thr
Asn Val Leu Gly Glu Ala Lys Lys Leu Asn Glu Ser Gln Ala Pro
Lys Ala Asp Asn Asn Phe Asn Lys Glu Gln Gln Asn Ala Phe Tyr
Glu Ile Leu Asn Met Pro Asn Leu Asn Glu Glu Gln Arg Asn Gly
Phe Ile Gln Ser Leu Lys Asp Asp Pro Ser Gln Ser Ala Asn Leu
Leu Ser Glu Ala Lys Lys Leu Asn Glu Ser Gln Ala Pro Lys Ala
Asp Asn Lys Phe Asn Lys Glu Gln Gln Asn Ala Phe Tyr Glu Ile
Leu His Leu Pro Asn Leu Asn Glu Glu Gln Arg Asn Gly Phe Ile
Gln Ser Leu Lys Asp Asp Pro Ser Gln Ser Ala Asn Leu Leu Ala
Gln Ala lys Lys Leu Asn Asp Ala Gln Ala Pro Lys Ala Asp Asn
Lys Phe Asn Lys Glu Gln Gln Asn Ala Phe Tyr Glu Ile Leu His
Leu Pro Asn Leu Thr Glu Glu Gln Arg Asn Gly Phe Ile Gln Ser
Leu Lys Asp Asp Pro Gly Asn Ser Lys Gly Gly Leu Asn Met Leu
Pro Ply Val Gly Leu Thr Pro Ser Ala Ala Gln Thr Ala Arg Gln
His Pro Lys Met His Leu Ala His Ser Asn Leu Lys Pro Ala Ala
His Leu Ile Gly Asp Pro Ser Lys Gln Asn Ser Leu Leu Trp Arg
Ala Asn Thr Asp Arg Ala Phe Leu Gln Asp Gly Phe Ser Leu Ser
Asn Asn Ser Leu Leu Val Pro Thr Ser Gly Ile Tyr Phe Val Tyr
Ser Gln Val Val Phe Ser Gly Lys Ala Tyr Ser Pro Lys Ala Thr
Ser Ser Pro Leu Tyr Leu Ala His Glu Val Gln Leu Phe Ser Ser
Gln Tyr Pro Phe His Val Pro Leu Leu Ser Ser Gln Lys Met Val
Tyr Pro Gly Leu Gln Glu Pro Trp Leu His Ser Met Tyr His Gly
Ala Ala Phe Gln Leu Thr Gln Gly Asp Gln Leu Ser Thr His Thr
Asp Gly Ile Pro His Leu Val Leu Ser Pro Ser Thr Val Phe Phe -continued Gly Ala Phe Ala Leu.

4. DNA coding for a fused protein comprising a polypeptide containing an antibody binding site of protein A and polypeptide of lymphotoxin, and having anti-cancer action of lymphotoxin and an ability to bind to the Fc domain of an antibody.

5. DNA according to claim 4, having the following nucleic acid sequence:

ATG GAA CAA CGC ATA ACC CTG AAA GAA GCT TGG
GAT CAA CGC AAT GGT TTT TAC CAA AGC CTT AAA
GAT GAT CCA AGC CAA AGT GCT AAC GTT TTA GGT
GAA GCT CAA AAA CTT AAT GAC TCT CAA GCT CCA
AAA GCT GAT GCG CAA CAA AAT AAC TTC AAC AAA
GAT CAA CAA AGC GCC TTC TAT GAA ATC TTG AAC
ATG CCT AAC TTA AAC GAA GCG CAA CGT AAC GGC
TTC ATT CAA AGT CTT AAA GAC GAC CCA AGC CAA
AGC ACT AAC GTT TTA GGT GAA GCT AAA AAA TTA
AAC GAA TCT CAA GCT CCG AAA GCT GAT AAC AAT
TTC AAC AAA GAA CAA CAA AAT GCT TTC TAT GAA
ATC TTG AAT ATG CCT AAC TTA AAC GAA GAA CAA
CGC AAT GGT TTC ATC CAA AGC TTA AAA GAT GAC
CCA AGC CAA AGT GCT AAC CTA TTG TCA GAA GCT
AAA AAG TTA AAT GAA TCT CAA GCA CCG AAA GCG
GAT AAC AAA TTC AAC AAA GAA CAA CAA AAT GCT
TTC TAT GAA ATC TTA CAT TTA CCT AAC TTA AAC
GAA GAA CAA CGC AAT GGT TTC ATC CAA AGC CTA
AAA GAT GAC CCA AGC CAA AGC GCT AAC CTT TTA
GCA GAA GCT AAA AAG CTA AAT GAT GCT CAA GCA
CCA AAA GCT GAC AAC AAA TTC AAC AAA GAA CAA
CAA AAT GCT TTC TAT GAA ATT TTA CAT TTA CCT
AAC TTA ACT GAA GAA CAA CGT AAC GGC TTC ATC

-continued

CAA AGC CTT AAA GAC GAT CCG GGG AAT TCA AAA
GGA GGT TTA AAT ATG CTC CCG GGT GTT GGT CTT
ACT CCA TCA GCT GCC CAG ACT GCC CGT CAG CAC
CCC AAG ATG CAT CTT GCC CAC AGC AAC CTC AAA
CCT GCT GCT CAC CTC ATT GGA GAC CCC AGC AAG
CAG AAC TCA CTG CTC TGG AGA GCA AAC ACG GAC
CGT GCC TTC CTC CAG GAT GGT TTC TCC TTG AGC
AAC AAT TCT CTC CTG GTC CCC ACC AGT GGC ATC
TAC TTC GTC TAC TCC CAG GTG GTC TTC TCT GGG
AAA GCC TAC TCT CCC AAG GCC ACC TCC TCC CCA
CTC TAC CTG GCC CAT GAG GTC CAG CTC TTC TCC
TCC CAG TAC CCC TTC CAT GTG CCT CTC CTC AGC
TCC CAG AAG ATG GTG TAT CCA GGG CTG CAG GAA
CCC TGG CTG CAC TCG ATG TAC CAC GGG GCT GCG
TTC CAG CTC ACC CAG GGA GAC CAG CTA TCC ACC
CAC ACA GAT GGC ATC CCC CAC CTA GTC CTC AGC
CCT AGT ACT GTC TTC TTT GGA GCC TTC GCT CTG.

6. A plasmid comprising DNA coding for a fused protein comprising a popypeptide containing an antibody binding site of protein A and a polypeptide of lymphotoxin, and having anti-cancer action of lymphotoxin and an ability to bind to the Fc domain of an antibody.

7. A plasmid according to claim 6, wherein the plasmid is designated as pPRALT1.

8. *Escherichia coli* transformed with a plasmid comprising a DNA coding for a fused protein comprising a polypeptide containing an antibody binding site of protein A and a polypeptide of lymphotoxin, and having anti-cancer action of lymphotoxin and an ability to bind to the Fc domain of an antibody.

9. A process for production of a fused protein comprising a polypeptide containing an antibody binding site of protein A and a polypeptide of lymphotoxin, and anti-cancer action of lymphotoxin and an ability to bind to the Fc domain of an antibody, characterized by culturing *Escherichia coli* transformed with a plasmid comprising DNA coding for said protein, and obtaining said protein from the culture product.

* * * * *